United States Patent [19]

Barri et al.

[11] Patent Number: 4,654,316

[45] Date of Patent: Mar. 31, 1987

[54] SELECTIVE DEALUMINATION OF ZEOLITES

[75] Inventors: Sami A. I. Barri, London; Timothy K. McNiff, Weybridge, both of England

[73] Assignee: The British Petroleum Company p.l.c., London, England

[21] Appl. No.: 762,054

[22] Filed: Aug. 2, 1985

[30] Foreign Application Priority Data

Aug. 9, 1984 [GB] United Kingdom ................. 8420205

[51] Int. Cl.$^4$ .......................... B01J 29/06; B01J 29/28
[52] U.S. Cl. ......................................... 502/61; 502/85; 423/112
[58] Field of Search ..................... 502/61, 85; 423/112

[56] References Cited

U.S. PATENT DOCUMENTS 4,487,843 12/1984 Telford et al. ........................ 502/61

FOREIGN PATENT DOCUMENTS 0086543  8/1983  European Pat. Off. .
0095846 12/1983  European Pat. Off. .
0101316  2/1984  European Pat. Off. .

OTHER PUBLICATIONS

Zeolite Molecular Sieves, Donald W. Breck, John Wiley & Sons, N.Y. 1974, Chapter Seven, pp. 529–590.

*Primary Examiner*—Carl F. Dees
*Attorney, Agent, or Firm*—Brooks, Haidt, Haffner & Delahunty

[57] ABSTRACT

This invention relates to a process for selective dealumination, particularly surface dealumination of zeolites by sequential ion-exchange and calcination. The process is selective in the sense that the aluminium atoms within the pore structure of the zeolite remain virtually intact.

The surface dealuminated zeolites can be used, after loading with a gallium compound, as catalysts in hydrocarbon conversion reactions.

15 Claims, No Drawings

SELECTIVE DEALUMINATION OF ZEOLITES

The present invention relates to a process for selective dealumination, particularly surface dealumination of zeolites by sequential ion-exchange and calcination.

Calcination of zeolites to achieve a degree of dealumination thereby modifying the activity thereof is well known. Such methods are described for instance in EP No. 95305 and in the artices by Kerr, G. T., in J. Phys. Chem. 71, 4155 (1967) and by Scherzer, J. in J. Catalysis, 54, 285-288 (1978).

One of the major drawbacks of the prior art dealumination techniques is that they remove aluminium atoms from the entire framework of the zeolite i.e. both the external surface and the internal pores within the zeolite. Whilst removal of the aluminium atoms from the external surface is desirable to moderate non-shape-selective activity of the zeolite, the removal of aluminium atoms from within the pore structure is undesirable because it reduces the internal acid sites and hence a reduction in catalytic activity in the shape-selective environment of the zeolite pores. Removal of internal aluminium atoms from within the pores can also cause partial destruction of the zeolite pore structure which is detrimental to the zeolite.

It is therefore an object of the present invention to selectively achieve surface dealumination of the zeolite without adversely affecting the internal acid sites or pore structure of the zeolite.

Accordingly the present invention is a process for surface dealumination of a zeolite to improve the catalyst selectivity thereof for hydrocarbon conversion reactions, said zeolite containing in the framework a first set of ion-exchangeable cations and having a pore size which is incapable of allowing to pass therethrough a second set of cations said process comprising:

(a) refluxing the zeolite with an aqueous solution of metal cations capable of (i) entering the zeolite pores and (ii) exchanging with the first set of cations in the framework until substantially all the first set of cations within the pores have been replaced by the metal cations, (b) refluxing the metal cation exchanged zeolite from step (a) with an aqueous solution of the second set of cations which are capable of thermal decomposition into vapourisable components until substantially all of the metal cations on the external surface of the zeolite have been replaced by the second set of cations, (c) calcining the second set cation exchanged zeolite from step (b) at elevated temperature so as to thermally decompose the second set cations, and (d) contacting the calcined zeolite from step (c) with an aqueous solution of a third set of cations capable of exchanging with the internal metal cations introduced therein by step (a) until substantially all of the metal cations have been replaced with protons or ions capable of giving rise to protons upon subsequent thermal decomposition.

The first set of cations referred to herein are those present in the framework of the zeolite e.g. organic cations, inorganic cations and/or protons and these may be present in the internal pores, on the external surface or both. For instance these may be protons, alkali metal cations and/or template cations which are present in the as-synthesised zeolite or any cations which may have been accidentally or by design introduced into the zeolite framework prior to the commencement of the actual process of surface dealumination. In order to ensure that cations on the zeolite are of a uniform type prior to exchange with the second set of cations and in order to protect the internal acid sites of the zeolite during subsequent dealumination by calcination it is necessary to exchange the first set of cations on the zeolite with a metal cation. These metal cations exchange with all the framework cations, both external and internal, in the zeolite by virtue of their ability to enter readily the pores within the zeolite. Examples of metal cations which may be exchanged with the first set of cations include alkali metal cations, cations of Groups II and III of the Periodic Table and lower valent cations of the transition metals. Of these the alkali metal cations, especially sodium ions are preferred.

The ion-exchange with the metal cations is carried out by refluxing the parent zeolite with an aqueous solution of the metal cation until substantially all the first set cations within the pores of the zeolite have been exchanged for the metal cations. The completion of this ion-exchange step can be detected by atomic absorption spectroscopy of the refluxing solution.

After the metal ion-exchange step is completed, the exchanged product may, if desired, be washed with an aqueous solvent to remove any surplus unexchanged metal ions therefrom and then dried.

The metal ion-exchanged product, with or without the washing and drying step is then ready for exchange with the second set of cations referred to above.

The second set of cations referred to herein are those cations which are of a size/diameter greater than the pore size of the zeolite to be selectively dealuminated and which are readily decomposed thermally into vaporisable components. The second set cations therefore upon ion-exchange with the zeolite to be selectively dealuminated only exchange with the cations on the external surface of the zeolite. Specific examples of the second set of cations include those derived from organic bases such as trialkylamines, alkanolamines, and the like. When such cations are calcined after exchange with the cations on the external surface of the zeolite, they cause surface dealumination by known mechanisms. The second-set cation is preferably a tetra-alkyl ammonium ion, preferably a tetrapropyl ammonium ion. The second set cation exchange of the metal cation exchanged zeolite is carried out by refluxing the latter in an aqueous solution of the second set-cation. Since the second-set cation cannot enter the pores of the zeolite, the metal cations therein remain in tact during this stage and only the metal cations on the external surface undergo ion-exchange. The completion of the surface ion-exchange can be determined by atomic absorption spectroscopy of the refluxing solution.

Upon completion of the surface ion-exchange, the resultant exchanged product may be optionally washed with an aqueous solvent to remove any surplus unexchanged second-set cations from the zeolite surface. Thereafter the washed product may be dried. The product from the second-set cation exchange step is then calcined at an elevated temperature so as to thermally decompose the second-set cations into vaporous components leaving a zeolite which has protons on the surface and metal cations within the pores. The calcination step is preferably carried out at a temperature from 450° to 900° C. The calcination may be carried out at reduced, atmospheric or elevated pressures. The calcination is preferably carried out in an oxidising atmosphere. Examples of the oxidising atmosphere that may be used include air, steam, mixtures thereof and these may be optionally diluted with a carrier gas such as nitrogen. This step results in dealumination of the zeolite surface but the acid sites within the pores remain unaffected.

When the calcination step is completed, the product zeolite from that step is then subjected to a final treatment by contacting with a third set of cations capable of converting the internal metal cations, e.g. those within the pores of the zeolite, into protons or into ions capable of giving rise to protons upon subsequent thermal treatment. This may be achieved either by bringing the calcined product into contact with an aqueous solution of either an acid, preferably a mineral acid, or a salt readily decomposable thermally into vaporous components thereby giving rise to protons. An example of such a salt is ammonium nitrate. If an aqueous solution of a salt is used in the final ion-exchange to remove the internal metal cations, e.g. within the pores of the zeolite, the zeolite may have to be subjected to calcination to convert the cations from the salt within the pores into protons.

The resultant surface dealuminated zeolite with the internal acid sites and pore structure intact may be used as a catalyst or a catalyst support in the usual manner. For instance the surface deactivated zeolite may be loaded e.g. with a gallium oxide catalyst by known methods and may in addition be bound in an inert binder e.g. a silica matrix to improve the physical characteristics thereof.

The zeolites which have ion-exchangeable cations and pores which are incapable of allowing the second set of cations, e.g. a tetraalkyl ammonium ion, to pass through suitably have a silica to alumina molar ratio greater than 1.5:1, preferably greater than 20:1. Such zeolites are suitably selected from mordenites, ferrierites and zeolites of the MFI-type including the ZSM variety of zeolites designated by nos. 2, 3, 4, 5, 11, 12, 35, 38 and 48. Mordenites, ZSM-5, ZSM-11, ZSM-12, ZSM-35, ZSM-38 and ZSM-48 are preferred, and ZSM-5 is most preferred.

The zeolites selectively dealuminated as above are useful as catalyst or catalyst support for various hydrocarbon conversion reactions.

In particular, surface dealuminated zeolites of the present invention when loaded with a gallium catalyst are effective in converting $C_2$ to $C_5$ hydrocarbons especially ethane selectively to aromatic hydrocarbons. Typically, the conversion of ethane to aromatics may be carried out 600°–700° C., 0.1–10 bar pressure and 0.1–5 WHSV.

The dealuminated zeolites produced by the process of the present invention reduce significantly the proportion of heavy polycyclic aromatics formed during such a reaction.

The present invention is further illustrated with reference to the following Examples.

EXAMPLE 1

A sample of an MFI-type zeolite containing ammonium cations (zeolite prepared using $NH_3$ template according to the general process of our published EP 0030811-A) was exchanged with $Na+$ ions by refluxing for a period of 4 hours with a 1M solution of NaCl in water (pH of the solution ca. 10). The process was repeated to ensure complete exchange of the $NH_4+$ ions with $Na+$ ions. The exchanged zeolite was then washed with distilled water to remove any unexchanged cations and dried in air at 100° C The $Na+$ cations on the external surface of the zeolite were exchanged with tetrapropylammonium cations by refluxing with an aqueous solution of 0.5M tetrapropylammonium (TPA) bromide for a period of 4 hours. The $Na+$ ions within the pores remained intact.

The exchanged zeolite was then washed with distilled water to remove any unexchanged cations and dried in air at 100° C.

The zeolite was then calcined for 16 hours at a temperature of 600° C. in a still air atmosphere at atmospheric pressure. The temperature was raised from 100° C. to 600° C. at a rate of 100° C./hour. This caused vaporisation of the $TPA+$ ions and dealumination of the zeolite surface. The $Na+$ ions remaining within the pores of the surface-dealuminated zeolite were exchanged with ammonium ions by refluxing with 0.81M aqueous ammonium nitrate for 4 hours. The process was then repeated to ensure that all the $Na+$ ions had been exchanged. (The $NH_4+$ ions were converted to protons by thermal decomposition during the activation procedure of the finished catalyst).

The $NH_4+$ exchanged, surface-dealuminated zeolite was contacted with 20 ml of an 0.04M aqueous solution of gallium nitrate. This solution was just sufficient so as to wet the zeolite. The aqueous solvent was then removed by drying at 130° C. at sub-atmospheric pressure.

The gallium impregnated zeolite was then mixed with an equal weight of LUDOX AS 40 (Registered Trade Mark, 40% colloidal silica in water) to obtain a slurry which was dried for 16 hours at 100° C. to give a cake of zeolite in the inert silica binder. This was broken up and sieved to give catalyst particles which passed through a standard 12 mesh sieve but were retained by a 30 mesh sieve.

This procedure gave a final catalyst containing 0.72 wt % Ga.

6 ml of this catalyst (3.5g) was loaded into a vertical fixed bed reactor. The catalyst was contacted with nitrogen and the temperature of the reactor raised to 550° C. The catalyst was maintained under these conditions for 16 hours.

The catalyst was then contacted with $H_2$ at 600° C. for 0.5 hours prior to testing for ethane aromatisation by contacting with ethane at 625° C., 1 WHSV, 3 bar pressure.

The following results were obtained.

| Temp. °C. | Pressure Bar | WHSV $hr^{-1}$ | Contact Time S | Ethane Conv. wt % | Selectivity to aromatics wt % | Selectivity to $C_6$–$C_8$ wt % | Selectivity to $C_9+$ wt % |
|---|---|---|---|---|---|---|---|
| 625 | 3 | 1 | 7.3 | 36.3 | 58.0 | 47.0 | 11.0 |

Comparative Test 1—Unmodified MFI Catalyst

A sample of an MFI-type zeolite containing ammonium cations (zeolite prepared using ammonia as template according to the general process of our published EP 0030811-A) was impregnated with 20 ml of an 0.04M aqueous solution of Ga (NO$_3$)$_3$. This solution was just sufficient so as to wet the zeolite. The aqueous solvent was then removed by drying at 130° C., at sub-atmospheric pressure.

The gallium impregnated zeolite was then bound in an inert silica matrix as in Example 1 above and sieved to give catalyst particles which passed through a standard 12 mesh sieve but were retained by a 30 mesh sieve.

This procedure gave a final catalyst containing 0.8% Ga.

The catalyst was loaded into a vertical fixed bed reactor and was contacted with nitrogen while the temperature was raised to 550° C. This was maintained for 16 hours. The catalyst was then contacted with hydrogen at 600° C. for 0.5 hours prior to testing for the aromatisation of ethane at 625° C., 1 WHSV, and 3 bar pressure. The following results were obtained.

| Temp. °C. | Pressure Bar | WHSV hr$^{-1}$ | Contact Time S | Ethane Conv. wt % | Selectivity to aromatics wt % | Selectivity to C$_6$–C$_8$ wt % | Selectivity to C$_9$+ wt % |
|---|---|---|---|---|---|---|---|
| 625 | 3 | 1 | 7.2 | 27.5 | 41.7 | 24.4 | 17.3 |

EXAMPLE 2

A catalyst was prepared from an MFI-type zeolite containing ammonium cations by the procedure described in Example 1 above. The gallium loading was 0.95 wt %. This catalyst was placed in a vertical fixed bed reactor and was contacted with nitrogen as the temperature was raised to 550° C. The catalyst was maintained under these conditions for 16 hours. The catalyst was then contacted with hydrogen at 600° C. for 0.5 hours prior to testing for the aromatisation of ethane at 650° C., 0.5 WHSV and atmospheric pressure. The following results were obtained.

| Temp. °C. | Pressure Bar | WHSV hr$^{-1}$ | Contact Time S | Ethane Conv. wt % | Selectivity to aromatics wt % | Selectivity to C$_6$–C$_8$ wt % | Selectivity to C$_9$+ wt % |
|---|---|---|---|---|---|---|---|
| 650 | 1 | 0.5 | 5 | 62.8 | 59.2 | 33.0 | 26.2 |

Comparative Test 2—Unmodified MFI Catalyst

A catalyst was prepared from an MFI-type zeolite containing ammonium cations by the procedure described in comparative Test 1 above. The gallium loading was 0.9 wt %.

The catalyst was loaded into a vertical fixed bed reactor and was contacted with nitrogen as the temperature was raised to 550° C. These conditions were maintained for 16 hours. The catalyst was then contacted with hydrogen at 600° C. for 0.5 hours prior to testing for the aromatisation of ethane at 650° C., 0.5 WHSV and atmospheric pressure.

| Temp. °C. | Pressure Bar | WHSV hr$^{-1}$ | Contact Time S | Ethane Conv. wt % | Selectivity to aromatics wt % | Selectivity to C$_6$–C$_8$ wt % | Selectivity to C$_9$+ wt % |
|---|---|---|---|---|---|---|---|
| 650 | 1 | 0.5 | 5 | 60.8 | 60.7 | 27.0 | 33.6 |

Comparative Test 3—Unselective Dealumination

A sample of an MFI-type zeolite as described in Example 1 above was exchanged with NH$_4$+ ions by refluxing for a period of 4 hours with a 0.81M aqueous ammonium nitrate solution.

The zeolite was then placed in a horizontal tubular furnace the temperature of which was raised to 550° C. while contacting the zeolite with air flowing at 40 ml/min. The airflow was diverted through a water bath at 60° C. which gave a 20% v/v steam in air mixture on entering the furnace. The zeolite was contacted with this mixture for 2 hours with the temperature at 550° C. This caused dealumination within zeolite pores as well as the surface. The zeolite was then refluxed with 0.81M ammonium nitrate as previously.

The zeolite was impregnated with gallium nitrate solution and bound in an inert silica matrix as in Example 1.

The final catalyst contained 0.8 wt % Ga.

The bound catalyst was tested for ethane aromatisation as in Example 1.

The following result was obtained.

| Temp. °C. | Pressure Bar | WHSV* hr$^{-1}$ | Contact Time S | Ethane Conv. wt % | Selectivity to aromatics wt % | Selectivity to C$_6$–C$_8$ wt % | Selectivity to C$_9$+ wt % |
|---|---|---|---|---|---|---|---|
| 625 | 3 | 1 | 8.5 | 38.0 | 46.6 | 25.6 | 21.0 |

These results demonstrate the higher selectivity to $C_6$–$C_8$ aromatics (shape selective products) and lower selectivity to $C_9^+$ aromatics (products of non shape selective zeolite surfaces) obtained with the selectively dealuminated MFI catalysts (Examples 1 and 2) compared with the unmodified MFI catalysts (Comparative Tests 1 and 2) and the conventionally dealuminated MFI catalyst (Comparative Test 3).

We claim:

1. A process for the dealumination of a zeolite to improve the catalyst selectivity thereof for hydrocarbon conversion reactions, said zeolite containing in the framework a first set of ion-exchangeable cations and having a pore size which is incapable of allowing to pass therethrough a second set of cations said process comprising:
   (a) refluxing the zeolite with an aqueous solution of metal cations capable of (i) entering the zeolite pores and (ii) exchanging with the first set of cations in the framework until substantially all the first set of cations within the pores have been replaced by the metal cations,
   (b) refluxing the metal cation exchanged zeolite from step (a) with an aqueous solution of the second set of cations which are capable of thermal decomposition into vapourisable components until substantially all of the metal cations on the external surface of the zeolite have been replaced by the second set of cations,
   (c) calcining the second set cation exchanged zeolite from step (b) at elevated temperature so as to thermally decompose the second set cations, and
   (d) contacting the calcined zeolite from step (c) with an aqueous solution of a third set of cations capable of exchanging with the internal metal cations introduced therein by step (a) until substantially all of the metal cations have been replaced with protons or ions capable of giving rise to protons upon subsequent thermal decomposition.

2. A process according to claim 1 wherein the first set of cations are protons, alkali metal cations and/or template cations which are present in the as-synthesised zeolite or any cations introduced into the zeolite framework prior to the commencement of the actual process of surface dealumination.

3. A process according to claim 1 or 2 wherein the metal cations exchanged with the first set of cations are selected from alkali metal cations, cations of Groups II and III of the Periodic Table and lower valent cations of the transition metals.

4. A process according to claim 3 wherein the metal cations exchanged with the first set of cations are sodium ions.

5. A process according to claim 1 wherein the second set of cations are of a size/diameter greater than the pore size of the zeolite to be selectively dealuminated and which are readily decomposed thermally into vaporisable components.

6. A process according to claim 1 wherein the second set of cations are derived from an organic base.

7. A process according to claim 6 wherein the organic base is a trialkylamine or an alkanolamine.

8. A process according to claim 1 wherein the calcination step is carried out at a temperature from 450° to 900° C. in an oxidising atmosphere.

9. A process according to claim 1 wherein the internal metal cations are converted into protons by contacting the calcined product with an aqueous solution of a third set of cations derived from an acid or a salt readily decomposable thermally into vaporous components thereby giving rise to protons.

10. A process according to claim 9 wherein the acid is a mineral acid.

11. A process according to claim 9 wherein the salt capable of being thermally decomposed to protons is ammonium nitrate.

12. A process according to claim 1 wherein the zeolites which have ion-exchangeable cations and pores which are incapable of allowing the second set of cations to pass through have a silica to alumina molar ratio greater than 1.5:1.

13. A process according to claim 12 wherein the zeolite is selected from mordenites, ferrierites and zeolites of the MFI-type.

14. A process according to claim 13 wherein the zeolite is of the ZSM variety designated by nos. 2, 3, 4, 5, 11, 12, 35, 38 or 48.

15. A catalyst composition suitable for hydrocarbon conversion reaction said composition comprising a surface dealuminated zeolite according to claim 1 loaded with a gallium oxide catalyst.

* * * * *